United States Patent
Grunewald et al.

(10) Patent No.: US 6,784,427 B1
(45) Date of Patent: Aug. 31, 2004

(54) SAMPLES FOR TRANSMISSION ELECTRON MICROSCOPY

(75) Inventors: Wolfgang Grunewald, Chemnitz (DE); Alex Vogt, Buche (CH)

(73) Assignee: Bal-Tec AG, Balzers (LI)

(*) Notice: Subject to any disclaimer, the term of this patent is extended or adjusted under 35 U.S.C. 154(b) by 0 days.

(21) Appl. No.: 10/679,589

(22) Filed: Oct. 6, 2003

(30) Foreign Application Priority Data

Jul. 31, 2003 (CH) ............................................. 1335/03

(51) Int. Cl.⁷ ............................. G01N 1/28; G01N 1/32; H01J 37/26
(52) U.S. Cl. ...................... 250/311; 250/306; 250/307; 250/304; 250/492.2; 250/492.3
(58) Field of Search ................................. 250/311, 306, 250/307, 304, 492.2, 492.3

(56) References Cited

U.S. PATENT DOCUMENTS 5,004,920 A * 4/1991 Lee et al. .................... 250/304

2002/0000522 A1 * 1/2002 Alani ....................... 250/492.3

* cited by examiner

*Primary Examiner*—Nikita Wells
(74) *Attorney, Agent, or Firm*—Notaro & Michalos P.C.

(57) ABSTRACT

TEM samples are cut from a solid state material with length (l) and width (b) and with a front-side sample surface (7) onto which a curable adhesive of the flowable type is applied for fixing a fiber (2) with a diameter (d) aligned on the sample surface (7) in the longitudinal direction of the sample substantially centrally with respect to the width (b), with the adhesive (3) applied substantially over the entire area on the sample surface (7) and the fiber (2) aligning itself upon being placed onto the adhesive (3) and being wetted essentially along its entire length with the adhesive and the latter subsequently being cured. A simple and economical preparation of TEM samples with high quality is thereby made possible.

14 Claims, 1 Drawing Sheet

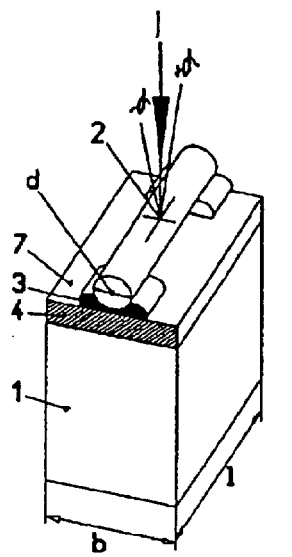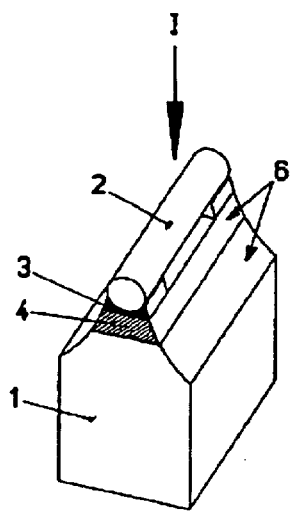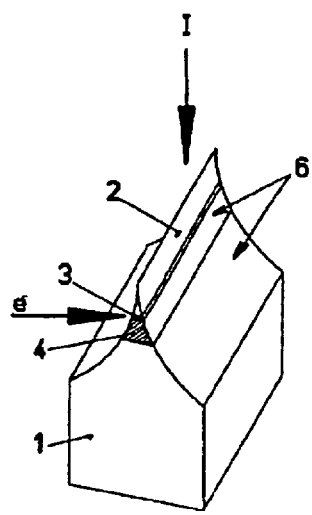
Fig. 1a (PRIOR ART)    Fig. 1b (PRIOR ART)    Fig. 1c (PRIOR ART)
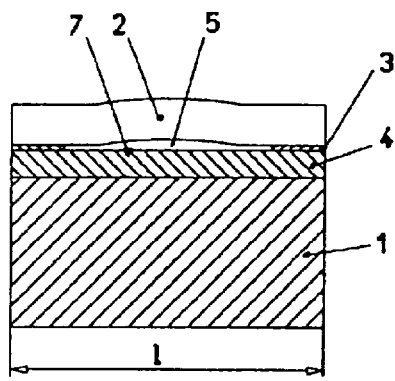
Fig. 1d (PRIOR ART)
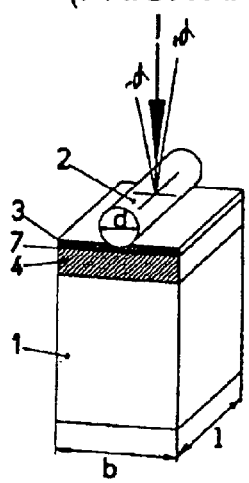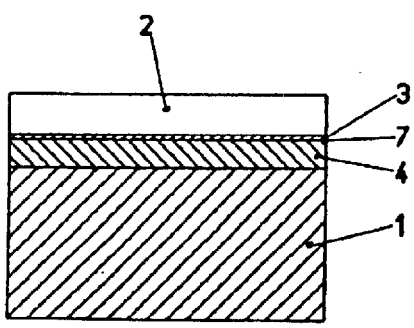
Fig. 2    Fig. 3

SAMPLES FOR TRANSMISSION ELECTRON MICROSCOPY

FIELD AND BACKGROUND OF THE INVENTION

The invention relates to a transmission electron microscopy (TEM) sample, as well as to a method for the production of such sample.

Samples for TEM can be prepared in various ways. To be able to examine samples with TEM, these must be thinned as defined, such that transmission through them is possible. Herein the quality of the sample determines essentially the quality of the image resolution. For this purpose the sample should be set uniformly to the correspondingly desired defined thickness through an appropriate etching process. It is important that in this etching process the sample structure is not changed by the process itself. To produce such a sample, a piece of the material to be examined is mechanically sawed out of the sample body and subsequently thinned further to the necessary or desired thickness by etching in order to be able to examine the sample subsequently with TEM. The wet-chemical etching method does not lead to the desired goal in this respect. For this reason, for high-quality TEM samples, the samples are currently worked by etching with an ion beam. As the ion beam is employed, for example, an argon ion beam with a diameter of approximately 1 mm.

Samples for transmission electron microscopy can by now be prepared in various ways. A method has been described in the literature, which is referred to as "wire shadow TEM cross section preparation technique". This so-called wire shadow method is described in Ultra Microscopy 70 (1997) 23–28, published by Elsevier Science B. V. Verlag 1997 under the title "Optimisation of the wire shadow TEM cross section preparation technique" by S. Senz, P. Kopperschmidt, E. Langer, H. Sieber, D. Hesse. These authors propose sawing a sample of the material to be examined from the solid body with a diamond saw. The sawed-out sample piece is rectangular, approximately 2–3 cm long and 200–300 $\mu$m wide. The width of the sample piece is additionally reduced to a value of 100 $\mu$m by mechanical working. In this process, the front-side face must not be damaged. The sample was, for example, cut from a semiconductor material such as silicon. After the sample has been sawed out of the sample body, placing, positioning and adhering takes place of an approximately 10 $\mu$m thick wire (shadow wire) or a fiber onto the front face of the sample, which represents the original sample surface. For this purpose, on both ends of the sample body a small amount of epoxy adhesive is applied onto the surface and subsequently the fiber, which has a length of a few mm, is centered on the sample surface and wetted with the adhesive. The adhesive should herein flow by capillary forces into the interspaces between the sample body and the fiber. The adhesive is subsequently cured. This entire process must be carried out highly precisely and is difficult of execution. After the adhesive has been cured, the sample is placed into a sample holder and in a vacuum receptacle the sample regions not shadowed are eroded through ion bombardment perpendicularly to the sample surface so far that an electron-transparent crest is generated in the margin of the shadow transversely to the sample surface. Under the ion bombardment the diameter of the shadow fiber is also decreased whereby the crest assumes a wedge form. The height of the crest can be affected as a function of the ion erosion rate of the material to be prepared, of the erosion rate of the shadow wire and of its diameter. To generate a smooth surface morphology on the side walls of the crest, a homogeneous material erosion is necessary. This can be attained through the selection of a suitably high ion acceleration voltage and also an additionally oscillating relative movement of the sample with respect to the incident ion beam. As a result of this cross section preparation an electron-transparent crest is generated with a length of a few hundred $\mu$m to mm. At the margin region of the crest close to the surface high-resolution, electron-optical characterizations are possible. One problem of the described technique of preparation comprises that it is very difficult to carry out. Preparation steps which determine the quality are the precise adhesion of the shadow fibers. In addition, the preparation of a sample takes several hours, which strongly reduces the economy of the process. For the reasons stated above, this form of preparation technique has so far not been widely accepted in the technical field.

SUMMARY OF THE INVENTION

The invention addresses the problem of eliminating the shortcomings of prior art. In particular a wire shadow or fiber shadow method will be realized, which makes possible realizing TEM samples at low expenditures, high reliability and good sample quality at simultaneously high economy.

The problem is solved according to the device of the invention while proceeding following the method of the invention.

According to the invention the TEM sample is cut from a solid state material such as a semiconductor, with the result of forming an elongated sample body with a front-side sample surface onto which an adhesive means, capable of flowing, is substantially applied over the entire surface. After a fiber is placed onto the adhesive, the latter is cured. When placing the fiber onto the surface, it becomes self-aligned in the longitudinal direction of the sample body on the sample surface and centered in the sample width through the occurring capillary forces. Due to the wetting of the sample surface with the adhesive, which covers substantially the entire area, the fiber can be wetted over its entire length and, with the aid of the capillary forces, can be positioned independently, such that precise placement is not necessary. On the other hand, through this type of adhesive application, structured sample surfaces are filled completely with the adhesive, such that no interspaces or voids are generated along the fiber, which would be highly negative for the quality of the TEM sample. When proceeding according to the teaching of prior art, such voids are not always entirely avoidable in the case of structured surfaces, since the adhesive is only applied at the sample ends and should become distributed with the aid of the capillary forces on the entire length between fiber and sample surface. Proceeding according to the invention is therefore especially suited for the preparation of samples of semiconductor materials such as are used in microelectronics. In this case samples are cut out of a semiconductor wafer such as for example silicon. Such a wafer is typically a few tenths mm thick and structured on the operative side and comprises differing layers through which the microelectronic structural elements are realized.

The fibers align themselves especially well without additional centering if the sample width is moreover sufficiently narrow. If the sample width is less than 20 $\mu$m, the effect of the independent alignment of the fiber on the sample surface proceeds especially well. It has been found that optimum results are attained if the sample width is in the range of 10 to 20 µm. The self-alignment effect of the fiber is still operative even if its diameter is slightly larger than the sample width, however, it is better if the fiber diameter is not greater than the sample width. It has been found that especially good results are obtained with a fiber diameter in the range of 5 to 20 µm. It is additionally favorable if the fiber covers at least half of the adhesive. As adhesive agents are suitable flowable adhesives, which after a certain time cure by themselves or are curable. Preferred are here epoxy adhesives. Especially suitable fiber materials are carbon or silicon carbide, which are produced in the form of a wire with a substantially circular cross section.

The sample prepared in this manner is now thinned by ion beam etching in a further treatment step. The direction of incidence of the ion beam is substantially perpendicular to the sample surface and directed onto the fiber. Through the shadow effect of the fiber a wedge-form sample is generated, which becomes transparent to electrons at the thinnest site. It is herein advantageous to move the ion beam back and forth through a specific angle relative to the sample within the plane perpendicular to the sample surface through the fiber. Etching takes place until the desired electron transparency for the TEM in the transverse direction to the crest has been reached. It is not absolutely necessary that the fiber is eliminated through the etching. It can remain or be etched away entirely or partially. It is advantageous to etch until the fiber has disappeared in one location. In this case, slight thickness differences of the sample crest are formed, and it is possible to select a favorable examination site for TEM.

The advantages of the method according to the invention comprise that a target preparation is readily possible. This means that the desired location for the examination of the sample can be precisely defined, for example with an accuracy in the pm range. In addition, the thin sample leads to low etching times in the range of one hour and to total preparation times of approximately two hours making the sample preparation extremely economical. According to prior art, for making samples for the target preparation, a time expenditure in the range of 3 to 10 hours is necessary. According to the present method according to the invention large clean electron-transparent sample areas can be produced which are several mm long. This means that the original structure of the material in the sample to be examined is changed only minimally or not at all, thus a low degree of surface amorphization or a small disturbance depth occurs in the material. This makes possible high fidelity to the original of the image in the TEM of the material to be examined.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

BRIEF DESCRIPTION OF THE DRAWINGS

In the following the invention will be explained in further detail by example and in conjunction with schematic drawings wherein:

FIG. 1a is a view of a sample with fiber adhered thereon according to prior art in three-dimensional representation;

FIG. 1b is a view of a sample with adhered fiber according to prior art partially etched off by an ion beam in three-dimensional representation;

FIG. 1c is a view of a sample with adhered fiber according to prior art etched off in the final state in three-dimensional representation;

FIG. 1d is a view of a sample with adhered fiber before etching according to prior art in longitudinal section;

FIG. 2 is a view of a sample according to the invention with fiber adhered over the entire area in longitudinal section; and FIG. 3 is a view of a sample according to the invention with fiber adhered over the entire area in longitudinal section.

DESCRIPTION OF THE PREFERRED EMBODIMENTS

A sample body is cut out of the sample material with a diamond saw, such that an elongated sample body 1 is formed with length l and width b, as is shown in FIG. 1a. If the sample is one cut from a microelectronic wafer, this sample 1 often has a structured surface 7, which can comprise additionally coatings 4 or layer systems 4. A fiber 2 with diameter d is adhered on the sample surface 7 with an adhesive 3. According to prior art the adhesive is applied on-center with respect to width b of sample 1 in the end regions of the sample length l and the fiber is carefully positioned centrally with respect to width b. According to prior art the sample width b should be approximately 100 µm and the adhesive 3 should only be applied in the region of fiber 2. This does not always ensure that the adhesive points 3 applied in the end region of sample 1 also spread by flowing completely between the fiber and the sample surface 7. Thereby, as shown in FIG. 1d, undesirable voids 5 are formed, especially in the case of structured sample surfaces 7, which degrade the sample quality or even make them unusable. In FIGS. 1a, b, c the progression of the subsequent etching process is depicted. The ion beam I is directed perpendicularly to the sample surface 7 onto fiber 2. FIG. 1a shows that the ion beam I can be moved back and forth in the manner of a pendulum through an angle ±α with respect to the perpendicular direction of incidence. This pendulum movement takes place in the plane perpendicular to the sample surface 7, which extends through the fiber 2. After a specific etching time, flanks 6 are formed through the material erosion of sample 1 and it can already be seen that a crest-like tapering of the sample develops, as is evident in FIG. 1b. In FIG. 1c the sample is shown in its final state. Sample 1 is now etched off by the ion beam to such an extent that a clear wedge-form formation is generated transversely to its length l. The etched flanks 6 on both sides of sample 1 now include an elongated crest which tapers to a point and in this region is transmissive to electrons for the TEM, which is depicted by $e^{31}$ and an arrow transversely to the longitudinal direction of the sample. In this state, the fiber 2 is also heavily etched off.

In contrast to the above described prior art, according to the invention, as shown in FIG. 2, the sample surface 7 is covered essentially completely with the adhesive 3, in order to fix the fiber 2 on the surface. With this method, the adjustment, or centering, of the fiber 2 takes place independently through the action of capillary forces. As an adhesive 3 a flowable adhesive has been found useful, which cures or is curable after the fiber 2 has been placed onto it. Especially suitable is here an epoxy adhesive 3, for example by Gattan Inc. 5933 Coronado Lane, Pleasanton, Calif. 94588 of type G1. Suitable fibers 2 are especially materials such as carbon or silicon carbide, although other materials can also be utilized. The ion etching rate of fiber 2 should preferably be lower than that of the sample material 1. Through appropriate selection of the fiber material the desired sputter yield (degree of sputtering) can be optimized for the process. The substantially complete wetting of the sample surface 7 with the adhesive 3 also ensures that between fiber 2 and sample 1 a complete connection over the entire length is attained without undesirable voids forming between them and that this is also the case with structured sample surfaces 7, as is depicted in FIG. 3. The self-alignment and positioning of fiber 2 on sample 1 through capillary forces is especially simple and favorable if the sample width b is substantially smaller than is proposed according to prior art. The sample width should, according to the invention, be less than 20 μm, preferably in the range of 10 to 20 μm. It is in addition favorable if the fiber diameter d does not project over the sample width b.

In an example a 20 μm wide sample was sawn from a semiconductor wafer and subsequently with an epoxy adhesive G1 by Gattan a SIC fiber of 15 μm thickness was adhered onto it. For this purpose, first, the adhesive was applied onto the sample surface and subsequently the fiber was placed onto it, which became self-aligned. The adhesive was cured at 100° C. within 5 minutes under atmospheric pressure. The sample was subsequently etched for one hour with an ion beam at a bombardment angle of 90° relative to the sample surface. The acceleration voltage of the ion beam was 6.5 kV and the ion current 1.8 mA. The ion beam was oscillated through ±50° in the plane perpendicular to the sample surface with respect to the angle of incidence of the ion beam. The result was a clean, high-quality crest-form sample, transparent to electrons, which makes possible imaging the original material quality in the TEM with a high degree of detail at simultaneously economic expenditures for the sample preparation.

While a specific embodiment of the invention has been shown and described in detail to illustrate the application of the principles of the invention, it will be understood that the invention may be embodied otherwise without departing from such principles.

What is claimed is:

1. A TEM sample cut from a solid state material with length (l) and width (b) and with a front-side sample surface (7), comprising a curable adhesive (3) of the flowable type and fixing a fiber (2) with diameter (d) on the sample surface (7) aligned in the longitudinal direction of the sample (1) substantially on-center with respect to the width (b), characterized in that the adhesive (3) is substantially applied over the entire area on the sample surface (7) and the fiber (2) is substantially fixed adhesively along its entire length.

2. A sample as claimed in claim 1, characterized in that the sample width (b) is maximally 20 μm.

3. A sample as claimed in claim 2, characterized in that the sample width (b) is in the range of 10 to 20 μm and the diameter (d) of the fiber (2) is not greater than the sample width (b).

4. A sample as claimed in claim 3, characterized in that the diameter (d) of the fiber (2) is in the range of 5 to 20 μm.

5. A sample as claimed in claim 4, characterized in that the wire fiber (2) covers at least one half of the adhesive (3).

6. A sample as claimed in claim 5, characterized in that the adhesive (3) is an epoxy adhesive.

7. A sample as claimed in claim 6, characterized in that the wire fiber (2) is comprised of carbon or silicon carbide.

8. A method for the preparation of a TEM sample cut from a solid state material with length (l) and width (b) and with a front-side sample surface (7) onto which a curable adhesive (3) of the flowable type is applied for fixing a fiber (2) with diameter (d) on the sample surface (7), aligned in the longitudinal direction of the sample (1) substantially centrally with respect to width (b), characterized in that the adhesive (3) is applied substantially over the entire area of the sample surface (7) and the fiber (2) with the adhesive (3) applied on it becomes self-aligned and is substantially over its entire length wetted with the adhesive (3), and that it is subsequently cured.

9. A method as claimed in claim 8, characterized in that the sample is cut to a width (b) of maximally 20 μm.

10. A method as claimed in claim 9, characterized in that the sample is cut to a width (b) in the range of 10 to 20 μm and the diameter (d) of the fiber (2) is not greater than the sample width (b).

11. A method as claimed in claim 10, characterized in that the diameter (d) of the fiber (2) is in the range of 5 to 20 μm.

12. A method as claimed in claim 11, characterized in that the fiber (2) covers at least half of the adhesive (3).

13. A method as claimed in claim 12, characterized in that as the adhesive (3) an epoxy adhesive is utilized.

14. A method as claimed in claim 13, characterized in that as the fiber material (2) carbon or silicon carbide is utilized.

* * * * *